United States Patent [19]

Niebes et al.

[11] Patent Number: 4,507,314

[45] Date of Patent: Mar. 26, 1985

[54] DRUG FOR TREATING AFFECTIONS PROVOKED BY A TOO HIGH HISTAMINE LEVEL, OF THE GASTRODUODENAL MUCOSA AND ALLERGIC AFFECTIONS

[75] Inventors: Paul J. Niebes, Grez-Doiceau; Daniel M. Matagne, Taviers; Etienne P. Hanon, Saint-Gilles; Joseph L. Roba, Dion-Valmont; Georges E. Lambelin, Forest, all of Belgium

[73] Assignee: Midit, Societe Fiduciaire, Vaduz, Liechtenstein

[21] Appl. No.: 515,500

[22] Filed: Jul. 20, 1983

[51] Int. Cl.³ .................. A61L 9/04; A61K 31/365; A61K 31/195
[52] U.S. Cl. ................................ 514/456; 424/45; 514/926
[58] Field of Search .............. 424/280, 45, 283, 319

[56] References Cited

U.S. PATENT DOCUMENTS 4,152,448  5/1979  Wardell ...................... 424/283
4,285,964  8/1981  Niebes ........................ 424/283

FOREIGN PATENT DOCUMENTS 742073  5/1970  Belgium ...................... 424/283

Primary Examiner—Frederick E. Waddell
Attorney, Agent, or Firm—Cushman, Darby & Cushman

[57] ABSTRACT

Drug for treating affections provoked by a too high histamine level in the body, for treating affections of the gastroduodenal mucosa and allergic affections, comprising the reaction product of (+)-catechin with at least one basic amino-acid, which is more particularly selected from the group consisting of L-lysine, L-arginine and L-ornithine.

6 Claims, No Drawings

DRUG FOR TREATING AFFECTIONS PROVOKED BY A TOO HIGH HISTAMINE LEVEL, OF THE GASTRODUODENAL MUCOSA AND ALLERGIC AFFECTIONS

This invention relates to a drug and a method for treating affections provoked by a too high histamine level in the body, affections of the gastroduodenal mucosa and allergic affections.

According to the invention the drug comprises the reaction product of (+)-catechin with at least one basic amino-acid.

According to a particular embodiment of the invention, said drug comprises the reaction product of (+)-catechin with said basic amino-acid and further at least one other organic or inorganic acid.

The amino-acid may be natural or not, such as, for example, lysine, arginine, ornithine, L-lysine, L-arginine and L-ornithine.

The inorganic acids may be, for example, hydrochloric acid, sulfuric acid or phosphoric acid and the organic acids may be aliphatic, cycloaliphatic, aromatic, araliphatic or heterocyclic carboxylic or sulphonic acids, such as, for example, acetic, propionic, glycolic, gluconic, lactic, tartaric, citric, ascorbic, glucuronic, glutamic, methanesulfonic, toluenesulfonic, malonic, galactaric, galacturonic, maleic, fumaric acids.

Based on new biochemical and pharmacological observations, it has been found that said reaction products of (+)-catechin and at least one basic amino-acid, and of (+)-catechin, one basic amino-acid and at least another organic or inorganic acid, are able to lower the histamine level in various tissues and cells, including gastric mucosa mast cells, peritoneal mast cells, leucocytes and lung tissue, and to inhibit the histamine release from mast cells.

It is known that the histamine present in human gastric mucosa is exclusively localized in the mastocyte cells and that said histamine has an important effect on the secretion of gastric acid and on the origin of gastroduodenal ulcers (K. Mohri, et.al., Agents and Actions, 8, 372, 1978).

Furthermore, it is well known that histamin release caused by allergens plays a major role in allergic affections.

Consequently, the above mentioned reaction products of (+)-catechin present great pharmaceutical interest for the treatment of gastroduodenal ulcers and affections of the gastric mucosa, of gastro-intestinal allergy and of allergic affections of the skin of the respiratory system.

Of particular interest for said treatments are reaction products of (+)-catechin and L-lysine or L-arginine and of (+)-catechin and L-lysine or L-arginine and a mineral acid, such as hydrochloric acid, or an organic acid, such as acetic acid, citric acid or ascorbic acid.

Examples of (+)-catechin derivatives which are particularly interesting are:

(+)-catechin hydrochlorolysinate
(+)-catechin ascorbolysinate
(+)-catechin lysinate.

The newly discovered pharmaceutical properties of said (+)-catechin derivatives have been proved by several studies in vitro, on animal models and on human beings, which are summarized hereafter.

Biochemical studies in vitro have indicated that (+)-catechin hydrochlorolysinate inhibits histidine decarboxylase extracted from rabbit stomach with an $IC_{50}$ of $10^{-4}M$.

Further studies, carried out in vitro, have shown that the release of histamine from rat peritoneal mastocytes, stimulated by the release inducer 48/80, is inhibited by (+)-catechin hydrochlorolysinate by 27% at a concentration of $10^{-50}M$.

The amount of released histamine has been measured after incubation of the cells at 37° C. during 10 minutes with either an amount of compound 48/80 determinated to obtain a release of 50%, either with such quantity of compound 48/80 in combination with the test substance.

The inhibiting activity of said (+)-catechin derivatives on histamine release from rat peritoneal mastocytes has been confirmed by in vivo studies. In these experiments (+)-catechin hydrochlorolysinate was administered per os to Sprague-Dawley rats, 3 times a day during 3 days, at a dose of 30 mg/kg.

After sacrifice the peritoneal mastocytes were incubated during 10 minutes at 37° C. in the presence of 0.5 μg/ml of compound 48/80, which induced 50% histamine release in the control group (6 rats per group). Compared to the controls the histamine release of the mastocytes of the treated group was decreased by 22%.

Further studies, made in vivo, indicated that intraperitoneal injection of (+)-catechin hydrochlorolysinate at 30 mg/kg, induces a decrease of 33% of the histamine content in rat stomach mucosa and of 38% in the lungs.

The effect of the (+)-catechin derivatives on the histamine content of stomach mucosa has been confirmed by clinical studies on human beings.

In this study, 4 groups of 10 healthy persons received per os in double blind either placebo, either 500 mg, 1000 mg or 1500 mg of (+)-catechin hydrochlorolysinate per day during 3 days. Biopsies were taken before and after the treatment. In the treated groups, a decrease of the histamine level of the mucosa of the fundus, of the corpus and of the antrum has been observed which is dose dependent and which reaches a 30% decrease at the highest dose. The number of mastocytes has decreased in the same way. In the placebo group, the histamine level remained constant in the three areas of the stomach.

Taking into account the histamine release inhibiting properties of said reaction products of (+)-catechin and a basic amino-acid and the known effect of histamine on the genesis of gastric ulcers, it was expected that the amino-acid derivatives of (+)-catechin present beneficial effects for the treatment of affections of the gastroduodenal mucosa.

The preventive and curative effect of said (+)-catechin derivatives has clearly been proved by studies on animal models, which are summarized here after.

The preventive effect of (+)-catechin hydrochlorolysinate and of (+)-catechin ascorbolysinate has been studied as follows:

(a) on ulcers induced by stress caused by immobilization: After one week adaptation to the environment, female rats, (30 animals per group, 5 per cage), were immobilised during 12 hours by wrapping them, under narcosis with ether, in a plaster bandage.

After sacrifice of the animals, the dissected stomach was visually inspected and the lesions of the mucosa were scored according to their number and their intensity.

(b) on ulcers induced by stress caused by cold: The experimental conditions are the same as the ones used in the study of ulcers induced by immobilisation, but in this model, stress was induced by placing the rats, one per cage, in a cold room at $-10°$ C. for 5 hours.

The products to be tested were administered, immediately before the test, by intraperitoneal injection of 2 ml of a freshly prepared saline solution. The doses tested varied from 0.1 to 50 mg/kg. The controls received 2 ml of saline.

The results obtained showed that treatment with amino-acid derivatives of (+)-catechin induced a significant and dose dependant decrease in the number of lesions of the stomach of stressed rats.

When expressed in terms of dry (+)-catechin, the $ED_{50}$ in the gastric ulcers induced in rats by immobilisation is:

for (+)-catechin ascorbolysinate: 1.5 mg/kg
for (+)-catechin hydrochlorolysinate: 5 mg/kg.

Similar results were obtained against cold induced ulcers in rats and guinea-pigs.

Furthermore, the preventive action of the catechin derivatives against stress induced gastric ulcers has been shown also after their administration by oral route.

The technique used consisted of oral administration to rats of 30 mg/kg of (+)-catechin hydrochlorolysinate, given as a suspension in a 1% aqueous solution of carboxymethylcellulose. The tested product was given 3 times a day during the 3 days preceding the experiment. The last administration was given 1 hour before immobilisation of the rats during 12 hours.

After sacrifice, inspection of the gastric mucosa revealed a significant decrease of the proportion of rats with severe lesions: from 38% for the control group to 15% for the treated group.

The curvative activity on gastro-duodenal mucosa of the amino-acid derivatives of (+)-catechin has been established on animal models by means of the following technique:

In rats fasted for 24 hours, necrosis of the gastric mucosa was induced by intra-gastric administration of acetic acid (1 ml at 20%) one hour before treatment.

As a suspension in an aqueous solution of 1% carboxymethylcellulose, (+)-catechin hydrochlorolysinate was administered orally twice a day during 5 days.

Accordingly the rats were sacrified, the stomach mucosa was photographed and the lesions were scored.

In these conditions, at a dose of 150 mg/kg, a significant curative effect was noted as a reduction of 50% of the number of animals with severe lesions.

The lowering effect on the histamine level of the gastric mucosa and the curvative activity on gastroduodenal ulcers of (+)-catechin hydrochlorolysinate have been confirmed in human beings in a double blind study, in which the aminoacid derivative of (+)-catechin has been compared to cimetidine.

Patients suffering from duodenal ulcer were treated daily either with 1500 mg (+)-catechin hydrochlorolysinate (11 patients) either with 800 mg cimetidine (10 patients) during 4 weeks. Photographs of the ulcer and biopsies of the stomach mucosa were taken before and after each week of treatment.

The results obtained with (+)-catechin hydrochlorolysinate confirmed the activity observed previously, since a decrease of the histamine levels and a decrease of the number of mastocytes in the fundus, corpus and antrum mucosa by ±20% has been measured. Also a decrease of the mean histamine level of the plasma from 0.7 (±0.3) ng/ml to 0.3 (±0.1) ng/ml has been observed. The decrease was observed after one week treatment and remained constant during the following 3 weeks of the treatment.

(+)-catechin hydrochlorolysinate has no effect on the intragastric pH.

In the other group cimetidine showed no notable effect or induced an increase, in some cases of more than 10% of the histamine levels in the stomach mucosa and in the plasma.

Further results, based on the measurements of the ulcer diameter, confirmed the curative properties of (+)-catechin hydrochlorolysinate on human duodenal ulcer: 7 patients out of 11 had fully recovered after 1 month of treatment. The ulcer diameter of the other patients had decreased significantly.

In further biochemical studies carried out in vitro it was found that amino-acid derivatives of (+)-catechin are effective inhibitors of antigen induced histamin release from leucocytes of persons who are sensitive to allergic affections provoked by pollen or house dust.

This activity of the catechin derivatives has clearly been established by the following technique: the leucocytes, preincubated during 10 minutes at 37° C. with hydrochlorolysinate of (+)-catechin, were treated with the allergin, pollen or house dust, during 30 minutes at 37° C. to activate the histamine release.

Then the histamin level was measured in the leucocyte suspension and the supernatant liquid and compared to the values obtained from the controls. Preincubation of the leucocytes by $10^{-5}M$ or $10^{-6}M$ hydrochlorolysinate of (+)-catechin resulted in a release inhibition of 45%.

The activity of amino-acid derivatives of (+)-catechin on the histamine level of lung tissue is shown by the following experiment: two groups of 10 female Sprague-Dawley rats received either placebo either 30 mg/kg (+)-catechin hydrochlorolysinate during 3 days, 3 times a day. The drug was administered per os as a suspension in carboxymethyl cellulose (1% in water). Five hours after the last treatment the rats were sacrified and the histamine level in the homogenized lung tissue has been determined. In the treated group a decrease of the histamine level of 38% compared to the control group has been measured.

Toxicological studies have shown that the considered amino-acid derivatives of (+)-catechin have extremely low toxicity.

The acute toxicity of (+)-catechin hydrochlorolysinate, administered per os in rat is over 6 g/kg in both sexes. No mortality was found up to this dose, which did not cause behavioural changes.

Subacute toxicity studies in rat and in Cynomolgus monkeys indicated that (+)-catechin hydrochlorolysinate is well tolerated at doses up to 1000 mg/kg administered daily and per os during 5 weeks to monkeys and during 6 weeks to rats.

Besides, (+)-catechin hydrochlorolysinate is free of mutagenic properties, as is proven by the results of the Ames test and by the absence of chromosomic aberrations on human lymphocytes in vitro.

The experimental results given above clearly demonstrate that the amino-acid derivatives of (+)-catechin, specified previously, exhibit important protective and curative activities on lesions of gastroduodenal mucosa and anti-allergic properties since they are able to lower the histamine content in various tissues and to decrease the histamine release from various cells.

Consequently, said compounds have great therapeutical value for the treatment of gastroduodenal ulcers and for the treatment of allergic affections of the respiratory system, such as asthma and rhinitis, of allergic contact dermatitis and urticaria, of gastro-intestinal allergy and of allied allergic diseases.

The catechin derivatives useful for this invention may be administered, in view of the intended therapeutical application, orally, parenterally, topically, rectally or as an aerosol in various galenic forms.

This comprises pharmaceutical compositions containing as active ingredient at least a minimal effective amount of at least one of said reaction products of (+)-catechin and L-lysine, L-arginine or L-ornithine and which may contain also diluents, carriers or excipients and/or other pharmaceutical active ingredients.

Thus for example the compositions to be administered orally can be liquids or solids and exist as tablets, sugar-coated pills, coated tablets, capsules, granules, powders, syrups or suspensions. The dry oral formulations comprise additives and excipients usually used in galenic pharmacy, inert diluents, desintegration agents, binders and lubricants, such as lactose, starch, talc, gelatin, stearic acid, cellulose and derivatives thereof, silicic acid, magnesium stearate, polyvinylpyrrolidone, calcium phosphate, calcium carbonate and the like.

The aqueous suspensions, the emulsions and the oily solutions are prepared in the presence of sweetening agents, such as dextrose or glycerol, flavouring agents, such as vanillin for example, and can also contain thickening agents, wetting agents, preservation agents.

The oily emulsions and solutions are prepared in an oil of vegetal or animal origin and can contain emulsifiers, flavouring, dispersing, sweetening and antioxidant agents. For parenteral administration, sterile water, an aqueous polyvinylpyrrolidone solution, peanut oil, ethyl oleate and the like are used as a vehicle. These aqueous or oily injectable solutions can contain thickening, wetting, dispersing and gelling agents.

For rectal administration, several galenic forms can be used as suppositories or rectal capsules or gels.

The catechin derivatives useful for treating and preventing gastroduodenal affections can be used alone or in combination with other pharmaceutical active compounds exerting a similar or a different activity.

Usual daily doses for oral and rectal administration of the (+)-catechin derivatives, may vary from 200 mg to 5 g, and are preferentially 1500 mg. Usual daily doses for parenteral administration of the (+)-catechin derivatives vary from 50 mg to 5 g and are preferentially 1500 mg.

For topical administration galenic forms such as, for example, creams, pastes, ointments, solutions, suspensions, emulsions or gels can be used and the usual concentration of active compound in said galenic forms may vary from 0.1% to 30%.

Hereafter, a few galenic formulations are described as non limitative examples in which the active compound is represented by A and in chosen from the following compounds:

(+)-catechin hydrochlorolysinate
(+)-catechin ascorbolysinate
(+)-catechin lysinate.

| Tablets | |
|---|---|
| A | 500 mg |
| Ac-Di-Sol | 90 mg |
| Aerosil 200 | 20 mg |
| Polyvinylpyrrolidone | 30 mg |
| Talc | 30 mg |
| A | 200 mg |
| Aerosil 200 | 12 mg |
| Talc | 12 mg |
| Ac-Di-Sol | 35 mg |
| Magnesium stearate | 1 mg |
| Suppositories | |
| A | 500 mg |
| Witepsol H 15 | 2500 mg |
| Injectable | |
| A | 20 mg |
| Benzylalcohol | 20 mg |
| Lysine | ad pH = 7.4 |
| aqua purificata | ad 1 ml. |
| Cream | |
| A | 10 mg |
| Glycerin | 2 g |
| Perhydrosqualene | 8 g |
| Liquid paraffin | 8 g |
| Solid paraffin | 6 g |
| Cetylstearyl alcohol | 4.5 g |
| Sodium cetylstearylsulfate | 0.5 g |
| Emulgine B-3 | 2 g |
| Aluminium stearate | 0.3 g |
| Citric acid | 0.1 g |
| Nipasept | 0.2 g |
| Distilled water | ad g 100 |

It has to be noted that the studies and tests referred to hereinabove are also valid for drugs comprising the reaction products of (+)-catechin with L-arginine or L-ornithine and possibly with another acid as defined hereinabove.

We claim:

1. A method for treating a disorder related to an undesirable high histamine level or to an undesirable high histamine release in the body, which comprises administering to a host in need of such treatment, an effective amount of the reaction product of (+)-catechin with L-lysine and with another acid selected from the group consisting of hydrochloric and ascorbic acid.

2. A method as claimed in claim 1 for treating lesions of the gastroduodenal mucosa.

3. A method as claimed in claim 1 for treating allergic affections of the gastroduodenal mucosa or of allergic gastroduodenal ulcers.

4. A method as claimed in claim 1 for treating allergic affections of the respiratory system.

5. A method as claimed in any of claims 1 to 4, which comprises administering said reaction product orally or rectally at a daily dose of 200 mg to 5 g, parenterally at a daily dose of 50 mg to 5 g, or topically or as an aerosol.

6. A method as claimed in claim 1 for treating gastroduodenal ulcers or allergies caused by histamine release.

* * * * *